(12) United States Patent
Kossmann et al.

(10) Patent No.: US 6,265,635 B1
(45) Date of Patent: Jul. 24, 2001

(54) DNA SEQUENCES CODING FOR ENZYMES CAPABLE OF FACILITATING THE SYNTHESIS OF LINEAR α-1,4 GLUCANS IN PLANTS, FUNGI AND MICROORGANISMS

(75) Inventors: Jens Kossmann, Golm; Volker Buttcher, Lauenforde; Thomas Welsh, Berlin, all of (DE)

(73) Assignee: Plantec Biotechnologie GmbH Forschung & Entwicklung, Potsdam (DE)

( * ) Notice: Subject to any disclaimer, the term of this patent is extended or adjusted under 35 U.S.C. 154(b) by 0 days.

(21) Appl. No.: 08/737,752

(22) PCT Filed: May 18, 1995

(86) PCT No.: PCT/EP95/01893

§ 371 Date: Feb. 27, 1997

§ 102(e) Date: Feb. 27, 1997

(87) PCT Pub. No.: WO95/31553

PCT Pub. Date: Nov. 23, 1995

(30) Foreign Application Priority Data

May 18, 1994 (DE) ................................. 44 17 879
Dec. 22, 1994 (DE) ................................. 44 47 388

(51) Int. Cl.$^7$ ............................ A01H 1/00; C12N 15/82; C12N 15/87; C07H 12/04
(52) U.S. Cl. ..................... 800/284; 536/23.6; 536/23.1; 536/23.74; 435/419; 435/410; 435/243; 435/252.3; 435/320.1; 435/468; 435/254.1; 435/254.11; 800/278; 800/290
(58) Field of Search .................. 536/23.6, 23.1, 536/23.74; 435/254.11, 252.3, 419, 410, 243, 320.1, 468; 800/278, 784, 290

(56) References Cited

FOREIGN PATENT DOCUMENTS

| | | |
|---|---|---|
| 4227061-A1 | 2/1994 | (DE) . |
| 4420223-C1 | 5/1995 | (DE) . |
| WO 89/12386 | 12/1989 | (WO) . |
| WO 90/02484 | 3/1990 | (WO) . |
| WO 92/11375 | 7/1992 | (WO) . |
| WO 92/14827 | 9/1992 | (WO) . |

OTHER PUBLICATIONS

Guibourdenche et al. Ann. Inst. Pasteur/Microbiol. 1986, vol. 137 B, pp. 177–185.*
Napoli et al. The Plant Cell. 1989. vol. 2: 278–289, 1989.*
G. Okada et al., "New Studies on Amylosucrase, a Bacterial α–D–Glucosylase That Directly Converts Sucrose to a Glycogen–like α–Glucan", *Journal of Biological Chemistry* 249:126–135 (1974).
C. R. MacKenzie et al., "Glycogen Synthesis by Amylosucrase From *Neisseria perflava*", *Canadian Journal of Microbiology* 23:1303–1307 (1977).
C. R. MacKenzie et al., "Glycogen Metabolism in the Genus *Neisseria*: Synthesis From Sucrose by Amylosucrase", *Canadian Journal of Microbiology* 24:357–362 (1978).
B. Y. Tao et al., "*Neisseria perflava* Amylosucrase: Characterization of Its Product Polysaccharide And a Study of Its Inhibition by Sucrose Derivatives", *Carbohydrate Research* 181:163–174 (1988).
F. R. van der Leij et al., "Expression of The Gene Encoding Granule Bound Starch Synthase After Introduction in an Amylose–Free And a Wildtype Potato (*Solanum Tuberosum*)", Abstract VIIth International Congress on Plant Tissue and Cell Culture, A5–28, Jun. 24 –Jun. 29, 1990.
M. J. M. Ebskamp et al., "Accumulation of Fructose Polymers in Transgenic Tobacco", *Biotechnology* 12:272–275 (1994).
I. M. van der Meer et al., "Fructan as a New Carbohydrate Sink in transgenic Potato Plants", *The Plant Cell* 6:561–570 (1994).

* cited by examiner

Primary Examiner—Phuong T. Bui
(74) Attorney, Agent, or Firm—Fish & Neave; James F. Haley, Jr.; Elinor K. Shin

(57) ABSTRACT

The invention relates to DNA sequences coding for proteins having the enzymatic activity of an amylosucrase which allows the synthesis of linear α-1,4 glucans from the substrate sucrose by bacteria, fungi and plants or in cell-free systems. The invention furthermore describes plasmids and bacteria containing these DNA sequences as well as processes for the production of plants and microorganisms capable of intracellularly or extracellularly expressing a polypeptide having amylosucrase activity. The invention furthermore relates to the production of pure fructose using proteins exhibiting the enzymatic activity of amylosucrase.

25 Claims, 2 Drawing Sheets

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
       (A) LENGTH: 2914 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Neisseria polysaccharea (vii) IMMEDIATE SOURCE:
       (A) LIBRARY: genomic library in pBluescriptII SK
       (B) CLONE: pNB2

(ix) FEATURE:
       (A) NAME/KEY: CDS
       (B) LOCATION:957..2867

(xi) SEQUENCE DESCRIPTION: SEQ ID NO: 1:

```
GAGTTTTGCG TTCCCGAACC GAACGTGATG CTTGAGCCGA ACACCTGTCC GGCAAGGCGG      60

CTGACCGCCC CCTTTTGCCC CATCGACATC GTAACAATCG GTTTGGTGGC AAGCTCTTTC     120

GCTTTGAGCG TGGCAGAAAG CAAAGTCAGC ACGTCTTCCG CGCTTTGCGG CATCACCGCA     180

ATTTTGCAGA TGTCCGCGCC GCAGTCCTCC ATCTGTTTCA GACGGCATAC GATTTCTTCT     240

TGCGGCGGCG TGCGGTGAAA CTCATGATTG CAGAGCAGGG CGGCGATGCC GTTTTTTTGA     300

GCATGCGCCA CGGCGCGCCG GACGGCGGTT TCGCCGGAAA AAAGCTCGAT ATCGATAATG     360

TCGGGCAGGC GGCTTTCAAT CAGCGAGTCG AGCAGTTCAA AATAATAATC GTCCGAACAC     420

GGGAACGAGC CGCCTTCGCC ATGCCGTCTG AACGTAAACA GCAGCGGCTT GTCGGGCAGC     480

GCGTCGCGGA CGGTCTGCGT GTGGCGCAAT ACTTCGCCGA TGCTGCCCGC GCATTCCAAA     540

AAATCGGCGC GGAACTCGAC GATATCGAAG GCAGGTTTT TGATTTGGTC AAGTACGGCG      600

GAAAGTACGG CGGCATCGCG GGCGACAAGC GGCACGGCGA TTTTGGTGCG TCCGCTTCCG     660

ATAACGGTGT TTTTGACGGT CAGGCTGGTG TGCATGGCGG TTGTTGCGGC TGAAAGGAAC     720

GGTAAAGACG CAATTATAGC AAAGGCACAG GCAATGTTTC AGACGGCATT TCTGTGCGGC     780

CGGCTTGATA TGAATCAAGC AGCATCCGCA TATCGGAATG CAGACTTGGC ACAAGCCCTG     840

TCTTTTCTAG TCAGTCCGCA GTTCTTGCAG TATGATTGCA CGACACGCCC TACACGGCAT     900

TTGCAGGATA CGGCGGCAGA CCGCCGGTCG GAAACTTCAG AATCGGAGCA GGCATC        956
```

| ATG | TTG | ACC | CCC | ACG | CAG | CAA | GTC | GGT | TTG | ATT | TTA | CAG | TAC | CTC | AAA | 1004 |
|-----|-----|-----|-----|-----|-----|-----|-----|-----|-----|-----|-----|-----|-----|-----|-----|------|
| Met | Leu | Thr | Pro | Thr | Gln | Gln | Val | Gly | Leu | Ile | Leu | Gln | Tyr | Leu | Lys | |
| 1 | | | | 5 | | | | | 10 | | | | | 15 | | |

| ACA | CGC | ATC | TTG | GAC | ATC | TAC | ACG | CCC | GAA | CAG | CGC | GCC | GGC | ATC | GAA | 1052 |
|-----|-----|-----|-----|-----|-----|-----|-----|-----|-----|-----|-----|-----|-----|-----|-----|------|
| Thr | Arg | Ile | Leu | Asp | Ile | Tyr | Thr | Pro | Glu | Gln | Arg | Ala | Gly | Ile | Glu | |
| | | | 20 | | | | | 25 | | | | | 30 | | | |

| AAA | TCC | GAA | GAC | TGG | CGG | CAG | TTT | TCG | CGC | CGC | ATG | GAT | ACG | CAT | TTC | 1100 |
|-----|-----|-----|-----|-----|-----|-----|-----|-----|-----|-----|-----|-----|-----|-----|-----|------|
| Lys | Ser | Glu | Asp | Trp | Arg | Gln | Phe | Ser | Arg | Arg | Met | Asp | Thr | His | Phe | |
| | | 35 | | | | | 40 | | | | | 45 | | | | |

```
CCC AAA CTG ATG AAC GAA CTC GAC AGC GTG TAC GGC AAC AAC GAA GCC      1148
Pro Lys Leu Met Asn Glu Leu Asp Ser Val Tyr Gly Asn Asn Glu Ala
    50                  55                  60

CTG CTG CCT ATG CTG GAA ATG CTG CTG GCG CAG GCA TGG CAA AGC TAT      1196
Leu Leu Pro Met Leu Glu Met Leu Leu Ala Gln Ala Trp Gln Ser Tyr
65                  70                  75                  80

TCC CAA CGC AAC TCA TCC TTA AAA GAT ATC GAT ATC GCG CGC GAA AAC      1244
Ser Gln Arg Asn Ser Ser Leu Lys Asp Ile Asp Ile Ala Arg Glu Asn
                85                  90                  95

AAC CCC GAT TGG ATT TTG TCC AAC AAA CAA GTC GGC GGC GTG TGC TAC      1292
Asn Pro Asp Trp Ile Leu Ser Asn Lys Gln Val Gly Gly Val Cys Tyr
            100                 105                 110

GTT GAT TTG TTT GCC GGC GAT TTG AAG GGC TTG AAA GAT AAA ATT CCT      1340
Val Asp Leu Phe Ala Gly Asp Leu Lys Gly Leu Lys Asp Lys Ile Pro
                115                 120                 125

TAT TTT CAA GAG CTT GGT TTG ACT TAT CTG CAC CTG ATG CCG CTG TTT      1388
Tyr Phe Gln Glu Leu Gly Leu Thr Tyr Leu His Leu Met Pro Leu Phe
130                 135                 140

AAA TGC CCT GAA GGC AAA AGC GAC GGC GGC TAT GCG GTC AGC AGC TAC      1436
Lys Cys Pro Glu Gly Lys Ser Asp Gly Gly Tyr Ala Val Ser Ser Tyr
145                 150                 155                 160

CGC GAT GTC AAT CCG GCA CTG GGC ACA ATA GGC GAC TTG CGC GAA GTC      1484
Arg Asp Val Asn Pro Ala Leu Gly Thr Ile Gly Asp Leu Arg Glu Val
                165                 170                 175

ATT GCT GCG CTG CAC GAA GCC GGC ATT TCC GCC GTC GTC GAT TTT ATC      1532
Ile Ala Ala Leu His Glu Ala Gly Ile Ser Ala Val Val Asp Phe Ile
                180                 185                 190

TTC AAC CAC ACC TCC AAC GAA CAC GAA TGG GCG CAA CGC TGC GCC GCC      1580
Phe Asn His Thr Ser Asn Glu His Glu Trp Ala Gln Arg Cys Ala Ala
                195                 200                 205

GGC GAC CCG CTT TTC GAC AAT TTC TAC TAT ATT TTC CCC GAC CGC CGG      1628
Gly Asp Pro Leu Phe Asp Asn Phe Tyr Tyr Ile Phe Pro Asp Arg Arg
            210                 215                 220

ATG CCC GAC CAA TAC GAC CGC ACC CTG CGC GAA ATC TTC CCC GAC CAG      1676
Met Pro Asp Gln Tyr Asp Arg Thr Leu Arg Glu Ile Phe Pro Asp Gln
225                 230                 235                 240

CAC CCG GGC GGC TTC TCG CAA CTG GAA GAC GGA CGC TGG GTG TGG ACG      1724
His Pro Gly Gly Phe Ser Gln Leu Glu Asp Gly Arg Trp Val Trp Thr
                245                 250                 255

ACC TTC AAT TCC TTC CAA TGG GAC TTG AAT TAC AGC AAC CCG TGG GTA      1772
Thr Phe Asn Ser Phe Gln Trp Asp Leu Asn Tyr Ser Asn Pro Trp Val
                260                 265                 270

TTC CGC GCA ATG GCG GGC GAA ATG CTG TTC CTT GCC AAC TTG GGC GTT      1820
Phe Arg Ala Met Ala Gly Glu Met Leu Phe Leu Ala Asn Leu Gly Val
                275                 280                 285

GAC ATC CTG CGT ATG GAT GCG GTT GCC TTT ATT TGG AAA CAA ATG GGG      1868
Asp Ile Leu Arg Met Asp Ala Val Ala Phe Ile Trp Lys Gln Met Gly
            290                 295                 300

ACA AGC TGC GAA AAC CTG CCG CAG GCG CAC GCC CTC ATC CGC GCG TTC      1916
Thr Ser Cys Glu Asn Leu Pro Gln Ala His Ala Leu Ile Arg Ala Phe
305                 310                 315                 320

AAT GCC GTT ATG CGT ATT GCC GCG CCC GCC GTG TTC TTC AAA TCC GAA      1964
Asn Ala Val Met Arg Ile Ala Ala Pro Ala Val Phe Phe Lys Ser Glu
                325                 330                 335

GCC ATC GTC CAC CCC GAC CAA GTC GTC CAA TAC ATC GGG CAG GAC GAA      2012
Ala Ile Val His Pro Asp Gln Val Val Gln Tyr Ile Gly Gln Asp Glu
                340                 345                 350

TGC CAA ATC GGT TAC AAC CCC CTG CAA ATG GCA TTG TTG TGG AAC ACC      2060
Cys Gln Ile Gly Tyr Asn Pro Leu Gln Met Ala Leu Leu Trp Asn Thr
            355                 360                 365
```

```
CTT GCC ACG CGC GAA GTC AAC CTG CTC CAT CAG GCG CTG ACC TAC CGC        2108
Leu Ala Thr Arg Glu Val Asn Leu Leu His Gln Ala Leu Thr Tyr Arg
    370                 375                 380

CAC AAC CTG CCC GAG CAT ACC GCC TGG GTC AAC TAC GTC CGC AGC CAC        2156
His Asn Leu Pro Glu His Thr Ala Trp Val Asn Tyr Val Arg Ser His
385                 390                 395                 400

GAC GAC ATC GGC TGG ACG TTT GCC GAT GAA GAC GCG GCA TAT CTG GGC        2204
Asp Asp Ile Gly Trp Thr Phe Ala Asp Glu Asp Ala Ala Tyr Leu Gly
                405                 410                 415

ATA AGC GGC TAC GAC CAC CGC CAA TTC CTC AAC CGC TTC TTC GTC AAC        2252
Ile Ser Gly Tyr Asp His Arg Gln Phe Leu Asn Arg Phe Phe Val Asn
        420                 425                 430

CGT TTC GAC GGC AGC TTC GCT CGT GGC GTA CCG TTC CAA TAC AAC CCA        2300
Arg Phe Asp Gly Ser Phe Ala Arg Gly Val Pro Phe Gln Tyr Asn Pro
            435                 440                 445

AGC ACA GGC GAC TGC CGT GTC AGT GGT ACA GCC GCG GCA TTG GTC GGC        2348
Ser Thr Gly Asp Cys Arg Val Ser Gly Thr Ala Ala Ala Leu Val Gly
450                 455                 460

TTG GCG CAA GAC GAT CCC CAC GCC GTT GAC CGC ATC AAA CTC TTG TAC        2396
Leu Ala Gln Asp Asp Pro His Ala Val Asp Arg Ile Lys Leu Leu Tyr
465                 470                 475                 480

AGC ATT GCT TTG AGT ACC GGC GGT CTG CCG CTG ATT TAC CTA GGC GAC        2444
Ser Ile Ala Leu Ser Thr Gly Gly Leu Pro Leu Ile Tyr Leu Gly Asp
                485                 490                 495

GAA GTG GGT ACG CTC AAT GAC GAC GAC TGG TCG CAA GAC AGC AAT AAG        2492
Glu Val Gly Thr Leu Asn Asp Asp Asp Trp Ser Gln Asp Ser Asn Lys
                    500                 505                 510

AGC GAC GAC AGC CGT TGG GCG CAC CGT CCG CGC TAC AAC GAA GCC CTG        2540
Ser Asp Asp Ser Arg Trp Ala His Arg Pro Arg Tyr Asn Glu Ala Leu
                515                 520                 525

TAC GCG CAA CGC AAC GAT CCG TCG ACC GCA GCC GGG CAA ATC TAT CAG        2588
Tyr Ala Gln Arg Asn Asp Pro Ser Thr Ala Ala Gly Gln Ile Tyr Gln
        530                 535                 540

GGC TTG CGC CAT ATG ATT GCC GTC CGC CAA AGC AAT CCG CGC TTC GAC        2636
Gly Leu Arg His Met Ile Ala Val Arg Gln Ser Asn Pro Arg Phe Asp
545                 550                 555                 560

GGC GGC AGG CTG GTT ACA TTC AAC ACC AAC AAC AAG CAC ATC ATC GGC        2684
Gly Gly Arg Leu Val Thr Phe Asn Thr Asn Asn Lys His Ile Ile Gly
                565                 570                 575

TAC ATC CGC AAC AAT GCG CTT TTG GCA TTC GGT AAC TTC AGC GAA TAT        2732
Tyr Ile Arg Asn Asn Ala Leu Leu Ala Phe Gly Asn Phe Ser Glu Tyr
                580                 585                 590

CCG CAA ACC GTT ACC GCG CAT ACC CTG CAA GCC ATG CCC TTC AAG GCG        2780
Pro Gln Thr Val Thr Ala His Thr Leu Gln Ala Met Pro Phe Lys Ala
            595                 600                 605

CAC GAC CTC ATC GGT GGC AAA ACT GTC AGC CTG AAT CAG GAT TTG ACG        2828
His Asp Leu Ile Gly Gly Lys Thr Val Ser Leu Asn Gln Asp Leu Thr
                610                 615                 620

CTT CAG CCC TAT CAG GTC ATG TGG CTC GAA ATC GCC TGA CGCACGCTTC        2877
Leu Gln Pro Tyr Gln Val Met Trp Leu Glu Ile Ala *
625                 630                 635

CCAAATGCCG TCTGAACCGT TTCAGACGGC ATTTGCG                                2914
```

(2) INFORMATION FOR SEQ ID NO: 2:

(i) SEQUENCE CHARACTERISTICS:
        (A) LENGTH: 636 amino acids
        (B) TYPE: amino acid
        (D) TOPOLOGY: linear

```
        (ii) MOLECULE TYPE: protein (xi) SEQUENCE DESCRIPTION: SEQ ID NO: 2:

Met Leu Thr Pro Thr Gln Gln Val Gly Leu Ile Leu Gln Tyr Leu Lys
  1               5                  10                  15

Thr Arg Ile Leu Asp Ile Tyr Thr Pro Glu Gln Arg Ala Gly Ile Glu
             20                  25                  30

Lys Ser Glu Asp Trp Arg Gln Phe Ser Arg Arg Met Asp Thr His Phe
         35                  40                  45

Pro Lys Leu Met Asn Glu Leu Asp Ser Val Tyr Gly Asn Asn Glu Ala
     50                  55                  60

Leu Leu Pro Met Leu Glu Met Leu Leu Ala Gln Ala Trp Gln Ser Tyr
 65                  70                  75                  80

Ser Gln Arg Asn Ser Ser Leu Lys Asp Ile Asp Ile Ala Arg Glu Asn
                 85                  90                  95

Asn Pro Asp Trp Ile Leu Ser Asn Lys Gln Val Gly Val Cys Tyr
                100                 105                 110

Val Asp Leu Phe Ala Gly Asp Leu Lys Gly Leu Lys Asp Lys Ile Pro
            115                 120                 125

Tyr Phe Gln Glu Leu Gly Leu Thr Tyr Leu His Leu Met Pro Leu Phe
        130                 135                 140

Lys Cys Pro Glu Gly Lys Ser Asp Gly Gly Tyr Ala Val Ser Ser Tyr
145                 150                 155                 160

Arg Asp Val Asn Pro Ala Leu Gly Thr Ile Gly Asp Leu Arg Glu Val
                165                 170                 175

Ile Ala Ala Leu His Glu Ala Gly Ile Ser Ala Val Val Asp Phe Ile
            180                 185                 190

Phe Asn His Thr Ser Asn Glu His Glu Trp Ala Gln Arg Cys Ala Ala
        195                 200                 205

Gly Asp Pro Leu Phe Asp Asn Phe Tyr Tyr Ile Phe Pro Asp Arg Arg
    210                 215                 220

Met Pro Asp Gln Tyr Asp Arg Thr Leu Arg Glu Ile Phe Pro Asp Gln
225                 230                 235                 240

His Pro Gly Gly Phe Ser Gln Leu Glu Asp Gly Arg Trp Val Trp Thr
                245                 250                 255

Thr Phe Asn Ser Phe Gln Trp Asp Leu Asn Tyr Ser Asn Pro Trp Val
            260                 265                 270

Phe Arg Ala Met Ala Gly Glu Met Leu Phe Leu Ala Asn Leu Gly Val
        275                 280                 285

Asp Ile Leu Arg Met Asp Ala Val Ala Phe Ile Trp Lys Gln Met Gly
    290                 295                 300

Thr Ser Cys Glu Asn Leu Pro Gln Ala His Ala Leu Ile Arg Ala Phe
305                 310                 315                 320

Asn Ala Val Met Arg Ile Ala Ala Pro Ala Val Phe Phe Lys Ser Glu
                325                 330                 335

Ala Ile Val His Pro Asp Gln Val Val Gln Tyr Ile Gly Gln Asp Glu
            340                 345                 350

Cys Gln Ile Gly Tyr Asn Pro Leu Gln Met Ala Leu Leu Trp Asn Thr
        355                 360                 365

Leu Ala Thr Arg Glu Val Asn Leu Leu His Gln Ala Leu Thr Tyr Arg
    370                 375                 380

His Asn Leu Pro Glu His Thr Ala Trp Val Asn Tyr Val Arg Ser His
385                 390                 395                 400
```

```
Asp Asp Ile Gly Trp Thr Phe Ala Asp Glu Asp Ala Ala Tyr Leu Gly
            405                 410                 415

Ile Ser Gly Tyr Asp His Arg Gln Phe Leu Asn Arg Phe Phe Val Asn
            420                 425                 430

Arg Phe Asp Gly Ser Phe Ala Arg Gly Val Pro Phe Gln Tyr Asn Pro
            435                 440                 445

Ser Thr Gly Asp Cys Arg Val Ser Gly Thr Ala Ala Leu Val Gly
    450                 455                 460

Leu Ala Gln Asp Pro His Ala Val Asp Arg Ile Lys Leu Leu Tyr
465                 470                 475                 480

Ser Ile Ala Leu Ser Thr Gly Leu Pro Leu Ile Tyr Leu Gly Asp
                485                 490                 495

Glu Val Gly Thr Leu Asn Asp Asp Trp Ser Gln Asp Ser Asn Lys
                500                 505                 510

Ser Asp Asp Ser Arg Trp Ala His Arg Pro Arg Tyr Asn Glu Ala Leu
            515                 520                 525

Tyr Ala Gln Arg Asn Asp Pro Ser Thr Ala Ala Gly Gln Ile Tyr Gln
530                 535                 540

Gly Leu Arg His Met Ile Ala Val Arg Gln Ser Asn Pro Arg Phe Asp
545                 550                 555                 560

Gly Gly Arg Leu Val Thr Phe Asn Thr Asn Asn Lys His Ile Ile Gly
                565                 570                 575

Tyr Ile Arg Asn Asn Ala Leu Leu Ala Phe Gly Asn Phe Ser Glu Tyr
            580                 585                 590

Pro Gln Thr Val Thr Ala His Thr Leu Gln Ala Met Pro Phe Lys Ala
            595                 600                 605

His Asp Leu Ile Gly Gly Lys Thr Val Ser Leu Asn Gln Asp Leu Thr
610                 615                 620

Leu Gln Pro Tyr Gln Val Met Trp Leu Glu Ile Ala
625                 630                 635
```

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(vi) ORIGINAL SOURCE:
        (A) ORGANISM: Neisseria polysaccharea (xi) SEQUENCE DESCRIPTION: SEQ ID NO: 3:

CTCACCATGG GCATCTTGGA CATC                                    24

(2) INFORMATION FOR SEQ ID NO: 4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(vi) ORIGINAL SOURCE:
        (A) ORGANISM: Neisseria polysaccharea

-continued (xi) SEQUENCE DESCRIPTION: SEQ ID NO: 4:

CTGCCATGGT TCAGACGGCA TTTGG                                                                 25

DNA SEQUENCES CODING FOR ENZYMES CAPABLE OF FACILITATING THE SYNTHESIS OF LINEAR α-1,4 GLUCANS IN PLANTS, FUNGI AND MICROORGANISMS

The present invention relates to recombinant DNA techniques for producing plants and microorganisms capable of intra- or extracellularly expressing a protein exhibiting amylosucrase activity and catalyzing the synthesis of linear α-1,4 glucans from sucrose. The present invention further relates to new DNA sequences and plasmids containing said DNA sequences which, after integration into a plant genome or after transformation in microorganisms, particularly bacteria or fungi, result in the expression of an enzyme catalyzing the synthesis of linear α-1,4 glucans from sucrose, as well as to transgenic organisms (i.e., plants, fungi and microorganisms) containing the above-mentioned DNA sequences.

Linear α-1,4 glucans are polysaccharides consisting of glucose monomers, the latter being exclusively linked to each other by α-1,4 glycosidic bonds. The most frequently occurring natural α-1,4 glucan is the amylose, a component of plant starch. Recently, more and more importance has been attached to the commercial use of linear α-1,4 glucans. Due to its physico-chemical properties amylose can be used to produce films that are colorless, odorless and flavorless, non-toxic and biologically degradable. Already today, there are various possibilities of application, e.g., in the food industry, the textile industry, the glass fiber industry and in the production of paper.

One has also succeeded in producing fibers from amylose whose properties are similar to those of natural cellulose fibers and which allow to partially or even completely replace them in the production of paper. Being the most important representative of the linear α-1,4 glucans, amylose is particularly used as binder for the production of tablets, as thickener of puddings and creams, as gelatin substitute, as binder in the production of sound-insulating wall panels and to improve the flow properties of waxy oils. Another property of the α-1,4 glucans, which recently has gained increasing attention, is the capability of these molecules to form inclusion compounds with organic complexers due to their helical structure. This property allows to use the α-1,4 glucans for a wide variety of applications. Present considerations relate to their use for the molecular encapsulation of vitamins, pharmaceutical compounds and aromatic substances, as well as their use for the chromatographic separation of mixtures of substances over immobilized linear α-1,4 glucans. Amylose also serves as starting material for the production of so-called cyclodextrins (also referred to as cycloamyloses, cyclomaltoses) which in turn are widely used in the pharmaceutical industry, food processing technology, cosmetic industry and analytic separation technology. These cyclodextrins are cyclic maltooligosaccharides from 6–8 monosaccharide units, which are freely soluble in water but have a hydrophobic cavity which can be utilized to form inclusion compounds.

Today, linear α-1,4 glucans are obtained in the form of amylose from starch. Starch itself consists of two components. One component forms the amylose as an unbranched chain of α-1,4 linked glucose units. The other component forms the amylopectin, a highly branched polymer from glucose units in which in addition to the α-1,4 links the glucose chains can also be branched via α-1,6 links. Due to their different structure and the resulting physico-chemical properties, the two components are also used for different fields of application. In order to be able to directly utilize the properties of the individual components, it is necessary to obtain them in pure form. Both components can be obtained from starch, the process, however, requiring several purification steps and involving considerable time and money. Therefore, there is an urgent need to find possibilities of obtaining both components of the starch in a uniform manner. To this end, so far starch-producing plants have been altered by breeding or by genetic manipulation to produce starch with an altered amylose/amolypectin proportion. While the normal amylopectin percentage of corn starch is e.g., 70%, one succeeded in establishing a maize variety (waxy maize) by breeding whose starch consists of almost 100% of amylopectin (Akatsuka and Nelson, 1966, J. Biol. Chem. 241:2280–2285). Furthermore, several maize varieties having an increased amylose content (60–70%) have been produced by breeding, e.g., the amylose extender and dull varieties (Wolf et al., 1955, J. Am. Chem. Soc. 77:1654–1659; Boyer et al., 1976, Die Stärke: 28:405–410). Other plant species were used to obtain varieties that synthesize uniform starches in form of amylopectin, e.g., rice (Sano, 1984, Theor. Appl. Genet. 68:467–473) and barley (Shannon and Garwood, 1984, in: Whistler, Bemiller, Paschall, Starch: Chemistry and Technology, Academic Press, Orlando, 2nd Edition: 25–86) or that synthesize highly amylose-containing starch (e.g., peas). In addition to the above approaches of classical breeding, approaches based on the genetic manipulation of starch-producing plants have been reported.

Visser et al. (1991, Mol. Gen. Genet. 255:289–296), for example, describe that potato varieties synthesizing substantially pure amylopectin starch can be obtained by anti-sense inhibition of the gene that codes for the starch-granule bound starch synthetase. WO 92/14827 discloses the production of potato plants which due to the anti-sense inhibition of the expression of the branching enzyme produce a starch having an increased amylose/amylopectin proportion. However, the plants described in WO 92/14827 do not produce a highly amylose-containing starch.

Despite numerous attempts and varied approaches, one has so far not succeeded in obtaining plants producing a pure amylose starch. Also, so far no possibility has been described to produce highly pure amylose or pure linear α-1,4 glucans by using other processes, e.g., genetically engineered microorganisms.

Furthermore, so far no DNA sequences have been found that encode enzymes that would be capable of catalyzing the synthesis of linear α-1,4 glucans in plants, fungi, microorganisms or in vitro.

It is therefore the object of the present invention to provide DNA sequences and processes that are capable of allowing the production of plants, fungi and microorganisms capable of synthesizing linear α-1,4 glucans.

The object of the present invention is achieved by the provision of the embodiments characterized by the patent claims.

The invention therefore relates to DNA sequences coding for proteins having the enzymatic activity of an amylosucrase.

Particularly, it relates to DNA sequences coding for a protein having the amino acid sequence indicated under Seq ID No. 1, and to the encoding DNA sequence indicated under Seq ID No. 1. The present invention furthermore relates to DNA sequences hybridizing to the above-mentioned sequences of the invention and coding for a protein having the enzymatic activity of an amylosucrase, as well as to DNA sequences which, due to the genetic code, are degenerate in comparison to the above-mentioned DNA sequences of the invention.

The term "hybridization" in this context means hybridization under conventional hybridization conditions, preferably under stringent conditions such as described by, e.g., Sambrook et al. (1989, Molecular Cloning, A Laboratory Manual, 2nd Edition, Cold Spring Harbor Laboratory Press, Cold Spring Harbor, N.Y.).

In another embodiment, the invention relates to DNA sequences coding for a protein having the enzymatic activity of an amylosucrase which are obtainable by a process comprising the following steps:

(a) preparing a genomic or a cDNA library on the basis of the genomic DNA or the mRNA of cells of an organism;

(b) transforming a suitable host with the library constructed in step (a);

(c) subjecting the transformed cells to iodine vapor;

(d) identifying the cells that are stained blue;

(e) isolating and cultivating the cells identified in step (d); and (f) isolating the genomic DNA insert or the cDNA insert from the transformed cells.

A suitable host as mentioned in step (b) is, e.g., *E. coli*.

In a preferred embodiment, the invention relates to DNA sequences coding for an amylosucrase from microorganisms, particularly gram negative microorganisms, preferably from bacteria of the species Neisseria and particularly preferred from *Neisseria polysaccharea*.

It is also possible to modify the DNA sequences of the invention by mutation or by a sequence alteration by insertion, deletion, substitution or recombination in order to alter certain properties of the protein to be expressed. One of these modifications is, inter alia, the deletion of the signal sequence ensuring secretion of the enzyme, and the inserts of other signal sequences or DNA sequences coding for transit peptides and thereby influencing the localization of the expressed protein.

The DNA sequences of the invention, in particular the DNA sequence of the invention indicated in Seq ID No. 1 or parts thereof, can be used to determine whether homologous DNA sequences are present in or are expressed by certain organisms. In order to achieve this DNA or mRNA samples of the individual organism are hybridized to a DNA sequence of the invention under appropriate hybridization conditions according to conventional methods. It is also possible to isolate according to standard techniques from the genome of various organisms homologous sequences which likewise encode amylosucrases or enzymes having similar properties by using a DNA sequence of the invention. In this context, homology means a sequence identity of at least 40% to 60%, preferably of more than 60%, particularly more than 80%, still more preferably a sequence identity of more than 95%. Homology furthermore means that the respective DNA sequences or encoded amino acid sequences are functionally and/or structurally equivalent. The sequences that are homologous to the sequences of the invention and that deviate from the DNA sequence or encoded amino acid sequence of the invention in one or more positions are regularly variations of said sequence which represent modifications having the same function. They may be naturally occurring variations, such a sequences of other organisms, or mutations. These mutations may occur naturally or may be achieved by specific mutagenesis. Furthermore, these variations may be synthetically produced sequences. All these DNA sequences are likewise comprised by the invention. The proteins encoded by the various variants of the DNA sequence of the invention share specific common characteristics, such as enzymatic activity, immunological reactivity, conformation etc., as well as physical properties such as electrophoretic mobility, chromatographic behavior, sedimentation coefficient, solubility, spectroscopic properties, stability etc.

In order to determine related DNA sequences, gene libraries of the organism to be examined must be obtained which are representative of the content of the genes of the organism or of the expression of genes in the organism or of a certain tissue of the organism. The first-mentioned type are genomic libraries, the latter cDNA libraries. Identification and isolation of homologous DNA sequences from such libraries is achieved by hybridization according to standard techniques (see, e.g., Sambrook et al., 1989, Molecular Cloning, A Laboratory Manual, 2nd Edition, Cold Spring Harbor Laboratory Press, Cold Spring Harbor, N.Y.). As hybridization probe DNA molecules can be used that exhibit exactly or substantially the DNA sequence indicated under Seq ID No. 1 or part of said sequence. The DNA fragments used as hybridization probes can also be synthetic DNA fragments which were prepared according to conventional DNA synthesis methods and are substantially identical to a sequence of the invention. Once the genes hybridizing to a DNA sequence of the invention have been identified and isolated, it is necessary to determine the sequence and to analyze the properties of the proteins encoded by said sequence.

The amylosucrase (also referred to as sucrose:1,4-α glucan 4-α-glucosyltransferase, E.C. 2.4.1.4) is an enzyme for which the following reaction scheme is suggested:

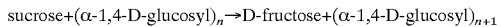

sucrose+(α-1,4-D-glucosyl)$_n$→D-fructose+(α-1,4-D-glucosyl)$_{n+1}$

This reaction is a transglucosylation. The products of this reaction are linear α-1,4 glucans and fructose. Cofactors are not required. Amylosucrase activity so far has been found only in few bacteria species, among them particularly the species Neisseria (MacKenzie et al., 1978, Can. J. Microbiol. 24:357–362) and the enzyme has been examined only for its enzymatic activity. According to Okada et al., the partially purified enzyme from *Neisseria perflava* upon addition of sucrose results in the synthesis of glycogen-like polysaccharides which are branched to a small extent (Okada et al., 1974, J. Biol. Chem. 249:126–135). Likewise, the intra- or extracellularly synthesized glucans of *Neisseria perflava* and *Neisseria polysaccharea* exhibit a certain degree of branching (Riou et al., 1986, Can. J. Microbiol. 32:909–911). Whether these branches are introduced by the amylosucrase or via another enzyme that is present in the purified amylosucrase preparations as contamination, has so far not been elucidated. Since an enzyme introducing branching has so far not been found, it is assumed that both the polymerization and the branching reactions are catalyzed by amylosucrase (Okada et al., 1974, J. Biol. Chem. 249:126–135). The enzyme that is expressed in a constitutive manner in Neisseria is extremely stable, binds very strongly to the polymerization products and is competitively inhibited by the product fructose (MacKenzie et al., 1977, Can. J. Microbiol. 23:1303–1307). The Neisseria species *Neisseria polysaccharea* secretes the amylosucrase (Riou et al., 1986, Can. J. Microbiol. 32:909–911) while in the other Neisseria species it remains in the cell. Enzymes having amylosucrase activity could only be detected in microorganisms. Plants are not known to have amylosucrases. According to the invention it could be shown that the product of the reaction catalyzed by amylosucrase are linear α-1,4 glucans that are not branched as has been assumed so far (see above).

The detection of the enzymatic activity of the amylosucrase can be achieved by detecting the synthesized glucans, as is described in Example 3, below. Detection is usually carried out by using a iodine stain. It is possible to identify bacterial colonies expressing amylosucrase by, e.g., treatment with iodine vapor. Colonies synthesizing the linear α-1,4 glucans are stained blue. The enzyme activity of the purified enzyme can be detected on, e.g., sucrose-containing agarose plates. If the protein is applied to such a plate and incubated for about 1 h or more at 37° C., it diffuses into the agarose and catalyzes the synthesis of linear glucans. The latter can be detected by treatment with iodine vapor. Furthermore, the protein can be detected in native polyacrylamide gels. After a native polyacrylamide gel electrophoresis the gel is equilibrated in sodium citrate buffer (50 mM, pH 6.5) and incubated over night in a sucrose solution (5% in sodium citrate buffer). If the gel is subsequently stained with Lugol's solution, areas in which proteins having amylosucrase activity are localized are stained blue due to the synthesis of linear α-1,4 glucans.

With the help of the DNA sequences of the invention it is possible to produce plants that are capable of producing pure amylose starch, i.e., linear α-1,4 glucans, and to modify starch-producing plants in such a way that they have higher starch yields and a simultaneously increased amylose/amylopectin proportion. The DNA sequences of the invention can be used to produce microorganisms and fungi, particularly yeasts, that are capable of producing an enzyme catalyzing the synthesis of linear α-1,4 glucans from sucrose. It is furthermore possible to produce at low production costs pure fructose syrup with the help of the DNA sequences of the invention or of the proteins encoded by them.

In another embodiment, the invention relates to recombinant DNA molecules, such as vectors, particularly plasmids, containing the DNA sequences of the invention or parts thereof, e.g., plasmid pNB2 which was deposited under DSM No. 9196. The invention particularly relates to recombinant DNA molecules in which a DNA sequence of the invention is linked to sequences ensuring expression of a protein having amylosucrase activity in microorganisms, fungi or plants, e.g., plasmids containing the following DNA sequences:

(a) an appropriate promoter being active in microorganisms which ensures that the coding sequence downstream thereof is transcribed in microorganisms, and (b) a DNA sequence coding for a polypeptide exhibiting amylosucrase activity and being linked to the promoter such that it allows formation of an RNA translatable into a polypeptide, or plasmids containing the following DNA sequences:

(a) an appropriate promoter being active in plants ensuring that the coding sequence downstream thereof is transcribed at the appropriate time or at an appropriate stage of development of a transgenic plant or in certain tissues of a transgenic plant, and (b) a DNA sequence coding for a polypeptide exhibiting amylosucrase activity and being linked to the promoter such that it allows formation of an RNA translatable into a polypeptide.

A further object of the invention are microorganisms, fungi and plants containing the recombinant DNA molecules of the invention.

A still further object of the invention are proteins having the enzymatic activity of an amylosucrase which are encoded by one of the DNA sequences of the invention, particularly those derived from microorganisms, preferably from gram negative microorganisms, specifically from microorganisms of the genus Neisseria and particularly preferred from *Neisseria polysaccharea*. An object of the invention are furthermore amylosucrases having a molecular weight of 63±20 kDA in gel electrophoresis, preferably of 63±15 kDA and most preferably of 63±10 kDa.

A further object of the invention are particularly proteins having the enzymatic activity of amylosucrase which exhibit the amino acid sequence depicted in Seq ID No. 1. The invention furthermore relates to proteins exhibiting amino acid sequences which are substantially identical to the amino acid sequence depicted in Seq ID No. 1 or which deviate from said sequence in one or more positions. The deviations preferably are conservative amino acid exchanges and the protein has the enzymatic activity of an amylosucrase. Thus, the invention furthermore relates to amylosucrases the amino acid sequence of which exhibits a high homology to the amino acid sequence indicated in Seq ID No. 1, in particular a homology of at least 70%, preferably of more than 80%, more preferred of more than 90% and particularly preferred a homology of at least 99%.

In a further embodiment, the invention relates to the use of the DNA sequences of the invention and of DNA molecules, particularly of plasmids, containing said DNA sequences for the transformation of procaryotic or eucaryotic cells as well as for the expression of an amylosucrase in procaryotic or eucaryotic cells, and also to a process for the production of the proteins of the invention by cultivating a microorganism containing a recombinant DNA molecule of the invention in an appropriate nutrient.

Specifically, the object of the present invention is a process for the production of plants which are capable of synthesizing linear α-1,4 glucans, characterized by introducing into plant cells a DNA sequence of the invention which comprises a region coding for a protein having the enzymatic activity of an amylosucrase linked to DNA sequences ensuring expression in plant cells and regeneration of whole plants from the transformed cells.

In addition, the present invention relates to a process for the production of plant cells and plants which are capable of synthesizing linear α-1,4 glucans, comprising the following process steps:

(a) producing an expression cassette having the following partial sequences:

(i) a promoter being active in plants and ensuring formation of an RNA in the respective target tissue or target cells;

(ii) at least one DNA sequence coding for a protein having the enzymatic activity of an amylosucrase and being fused to the promoter in sense orientation;

(iii) a signal being functional in plants for the transcription termination and polyadenylation of an RNA molecule;

(b) transferring the expression cassette into plant cells; and (c) regenerating intact whole plants from the transformed plant cells.

Useful promoters are those promoters that ensure a constitutive expression of the gene in all tissues of the plants such as the 35S promoter of the cauliflower mosaic virus (CaMV) as well as those that ensure expression only in certain organs or at certain times in the development of the plant. Known are promoters that ensure a specific expression in the tubers of potato plants, such as the B33 promoter (Liu et al, 1990, Mol. Gen. Genet. 223:401–406) or those that allow a specific expression in the roots of the sugar beet. Furthermore described are DNA sequences that allow a light-dependent and tissue-specific expression of DNA sequences downstream thereof in leaves (Orozco and Ogren, 1993, Plant Mol. Biol. 23:1129–1138).

The DNA sequence mentioned in process step (a) (ii) basically can be any DNA sequence comprising a coding region coding for a protein having the enzymatic activity of an amylosucrase. Useful DNA sequences are particularly DNA sequences derived from microorganisms, preferably from gram negative microorganisms, specifically of the genus Neisseria, and particularly from *Neisseria polysaccharea*. A preferred embodiment of the process of the invention contemplates the use of DNA sequences coding for a protein having the enzymatic activity of an amylosucrase, with the protein exhibiting the amino acid sequence depicted in Seq ID No. 1 or an amino acid sequence that is substantially identical to that. It is preferred to use DNA sequences that exhibit a high degree of homology to the DNA sequence indicated under Seq ID No. 1 and that encode an amylosucrase. Also DNA sequences can be used that can be derived from said sequences by substitution, insertion or deletion, as long as their enzymatic activity is not impaired. A particularly preferred embodiment of the process relates to the use of a DNA sequence that exhibits the nucleotide sequence indicated under Seq ID No. 1 or parts thereof, with the parts being long enough to encode a protein having the enzymatic activity of an amylosucrase.

According to the invention, the DNA sequence coding for an amylosucrase is linked in sense orientation to the promoter (3' end of the promoter to the 5' end of the coding sequence). This sequence can be modified before or after linkage to the transcription control elements (promoter and termination signal) in order to vary, if necessary, the properties of the polypeptide or its localization as is described infra in more detail. The DNA sequence depicted in Seq ID No. 1, e.g., encodes an extracellular amylosucrase. Secretion is ensured by a signal sequence comprising the 16 N terminal amino acid residues, encoded by the nucleotides 939 to 986 of the sequence depicted in Seq ID No. 1. Since such procaryotic signal sequences normally lead to a secretion of the protein also in plant cells, the expressed protein is transported to the apoplast of the plant when using the DNA sequence indicated under Seq ID No. 1. In order to express the enzyme in the cytosol of the plant cells, the signal sequence effecting secretion must be removed. If the enzyme to be expressed is to be directed to certain subcellular compartments such as chloroplasts, amyloplasts, mitochondria or the vacuole, the signal sequence effecting secretion must be replaced by a signal sequence or a sequence coding for a transit peptide which ensures the transport of the expressed protein to the respective compartment. Such sequences are known. For the transport into the plastids, e.g., the transit peptides of the precursor proteins of the small subunit of the ribulose bisphosphate carboxylase (RUBISCO) from potatoes (Wolter et al., 1988, Proc. Natl. Acad. Sci. USA 85:846–850) or of the acyl carrier protein (ACP) are useful. For the transport into the vacuole, e.g., the signal sequence of patatin can be used (Sonnewald et al., 1991, Plant J. 1:95–106). The sequences used must be fused in frame to the DNA sequence coding for the enzyme.

The transfer of the expression cassette constructed in process step (a) in plant cells is preferably carried out using plasmids, for example, binary plasmids. It is preferred to use techniques that ensure that the expression cassette is stably integrated into the genome of the transformed plant cell.

The process of the invention can basically be applied to any plant species. Both monocotyledonous and dicotyledonous plants are of interest. Transformation techniques have already been described for various monocotyledonous and dicotyledonous plant species.

The DNA sequences of the invention allow to modify plants such that they express proteins having the enzymatic activity of an amylosucrase, thereby allowing the synthesis of linear α-1,4 glucans in plants. Since linear α-1,4 glucans are identical to the amylose synthesized in plants in terms of their chemical structure, it is therefore possible to produce plants that synthesize the pure amylose and to modify starch-producing plants such that they synthesize a starch having an increased amylose proportion.

In most plants the photo assimilates formed in the course of photosynthesis are transported within the plant in form of sugars, more specifically mainly in the form of sucrose, to the respective target organs. Since the substrate for the polymerization reaction of the amylosucrase is sucrose, the process described above basically allows to modify all plants, both dicotyolodenous and monocotyledonous, with respect to an amylosucrase expression. Preferred are crop plants such as maize, rice, wheat, barley, sugar beet, sugar cane, tobacco, potatoes or cassava, but also fruit and vegetable species such as apples, plums, carrots or tomatoes.

The expression of an amylosucrase activity in plants can inter alia be used to change the viscosity of extracts obtained from the plants by synthesis of linear α-1,4 glucans. In this context, the tomato is of interest. By expression of an amylosucrase in the tomato fruit linear α-1,4 glucans are synthesized, thereby leading to an increased viscosity of the extracts that are obtained from these fruits.

Expression of amylosucrase is furthermore particularly advantageous in those organs of the plants that store large amounts of sucrose. Such organs are, e.g., the root of the sugar beet or the stem of the sugar cane. Since these plants normally do not synthesize any appreciable amounts of starch, the linear α-1,4 glucans synthesized by amylosucrase could be isolated in pure form from these plants.

The place of biosynthesis of the sucrose in plant cells is the cytosol. The place of storage, however, is the vacuole. During transport to the storage tissue of the sugar beet or the potato or during transport to the endospermium of seeds the sucrose has to pass the apoplast. Therefore, all three compartments, i.e., cytosol, vacuole and apoplast can be considered for the expression of the amylosucrase for the synthesis of linear glucans. In starch-producing plants such as potatoes or maize, in which starch synthesis and starch storage normally take place in the amyloplasts, an expression of the amylosucrase in the apoplast, in the cytosol or in the vacuole would lead to an additional synthesis of glucans in these compartments, thus meaning a considerable increase in yield. Since potatoes allow to separate the starch synthesized in the amyloplasts from the linear α-1,4 glucans synthesized by the amylosucrase in the apoplast, in the cytosol or in the vacuole during isolation of starch, one and the same plant could be used to obtain both starch and linear α-1,4 glucans.

Furthermore known are transgenic potato plants and maize plants in which due to an inhibition of the ADP glucose pyrophosphorylase by an antisense construct the starch synthesis in the tubers and grains, respectively, is completely inhibited. Instead, e.g., in potatoes soluble sugars, particularly sucrose and glucose, are accumulated in the tubers (Müller-Röber et al., 1992, EMBO J. 11:1229–1238; EP-A-0 455 316). By expression of an amylosucrase in the cytosol, the vacuole or the apoplast of these plants, i.e., in compartments where no branching enzymes are present, the synthesis of highly amylose-containing starch, i.e., starch mainly consisting of linear α-1,4 glucans, can be achieved. The reaction mechanism that is catalyzed by the amylosucrase is characterized by a glucose residue being directly transferred from sucrose to a linear glucan. In the biosynthesis of linear glucans from sucrose in plants the sucrose is first split into glucose and fructose which in turn are converted into the activated intermediate form ADP glucose. From the ADP glucose the glucose residue is transferred by the enzyme starch synthase to an already existing glucan, thereby releasing ADP. Conversion of sucrose into two molecules of ADP glucose requires several energy-consuming reactions. Therefore, the energy balance of the reaction catalyzed by the amylosucrase in comparison to the energy balance of the synthesis of amylose to sucrose in plant cells is substantially better, leading to an increased yield in synthesized glucans in plants expressing amylosucrase activity.

There are many cloning vectors available containing a replication signal for E. coli and a marker gene for the selection of transformed bacterial cells which can be used to prepare the introduction of foreign genes into higher plants. Examples of such vectors are pBR322, pUC series, M13mp series, pACYC184, etc. The desired sequence can be introduced into the vector at an appropriate restriction site. The plasmid obtained is used to transform E. coli cells. Transformed E. coli cells are cultivated in an appropriate medium and are then harvested and lysed. The plasmid is recovered. Methods of analysis generally used to characterize the obtained plasmid DNA are restriction analyses, gel electrophoresis, sequencing reactions and further methods known in biochemistry and molecular biology. After every manipulation the plasmid DNA can be cleaved and linked to other DNA sequences. Every plasmid DNA sequence can be cloned into the same or other plasmids. Many techniques are available for the introduction of DNA into a plant host cell. These techniques comprise the transformation of plant cells with T-DNA using Agrobacterium tumefaciens or Agrobacterium rhizogenes as transformation agents, the fusion of protoplasts, injection, electroporation of DNA, introduction of DNA by the bioballistic method as well as other possible techniques. Depending on the method of introduction of the desired genes into the plant cells, further DNA sequences may be required. If, e.g., the Ti or Ri plasmid is used for the transformation of the plant cell, at least the right border sequence, but often the right and left border sequence of the Ti and Ri plasmid T-DNA as flanking area must be linked with the genes to be introduced. If Agrobacteria are used for transformation, the DNA to be introduced must be cloned into special plasmids, either into an intermediate vector or into a binary vector. The intermediate vectors can be integrated by homologous recombination into the Ti or Ri plasmid of the Agrobacteria due to sequences that are homologous to sequences in the T-DNA. Said plasmid contains the vir region necessary for the transfer of the T-DNA. Intermediate vectors are not able to replicate in Agrobacteria. The intermediate vector can be transferred to Agrobacterium tumefaciens using a helper plasmid (conjugation). Binary vectors are able to replicate both in E. coli and in Agrobacteria. They contain a selection marker gene and a linker or polylinker flanked by the right and left T-DNA border regions. They can be directly transformed into Agrobacteria (Holsters et al., 1978, Mol. Gen. Genet. 163:181–187). The Agrobacterium serving as host cell should contain a plasmid carrying a vir region. The vir region is necessary for the transfer of the T-DNA to the plant cell. Additional T-DNA may be present. The thus transformed Agrobacterium is used to transform plant cells. The use of T-DNA for the transformation of plant cells has C been extensively examined and is sufficiently described in EP 120516; Hoekema, In: The Binary Plant Vector System, Offsetdrukkerij Kanters B. V., Alblasserdam, 1985, Chapter V; Fraley et al., Crit. Rev. Plant. Sci., 4:1–46 and An et al; 1985, EMBO J. 4:277–287. For the transfer of the DNA to the plant cells plant explants can expediently be cocultivated with Agrobacterium tumefaciens or Agrobacterium rhizogenes. From the infected plant material (e.g., pieces of leaves, stem segments, roots but also protoplasts or suspension-cultivated plant cells) whole plants can be regenerated on an appropriate medium which may contain antibiotics or biocides for the selection of transformed cells. The plants thus obtained can be screened for the presence of the introduced DNA. There are no specific requirements for the plasmids used for the injection and electroporation of DNA into plant cells. Simple plasmids such as pUC derivatives can be used. However, if it is intended to regenerate whole plants from the thus transformed cells, the presence of a selectable marker is required. Once the introduced DNA is integrated into the genome of the plant cell, it generally remains there stably and can also be found in the successor of the originally transformed cell. Normally it contains a selection marker which imparts to the transformed plant cells resistance to a biocide or an antibiotic such as kanamycin, G 418, bleomycin, hygromycin or gluphosinate etc. The individually selected marker should therefore allow for the selection of transformed cells over cells lacking the introduced DNA. The transformed cells grow within the cell as usual (cf., e.g., McCormick et al., 1986, Plant Cell Reports 5:81–84). These plants can be grown in the usual manner and can be cross-bred with plants possessing the same transformed genetic material or other genetic materials. The resulting hybrid individuals have the corresponding phenotypic properties. Two or more generations should be cultivated in order to make sure that the phenotypic features are stably retained and inherited. Furthermore, seeds should be harvested in order to make sure that the corresponding phenotype or other characteristics have been retained.

A further object of the invention are the modified plant cells and plants resulting from the above-mentioned process of the invention, particularly plant cells and plants containing a DNA sequence of the invention in combination with DNA sequences that allow the expression of the DNA sequence of the invention in plant cells. Said plant cells are characterized by expressing a protein having the enzymatic activity of an amylosucrase, thereby resulting in the synthesis of linear α-1,4 glucans in the cells or the plants. The transgenic plant cells and plants are furthermore characterized in that they contain a recombinant DNA molecule stably integrated into their genome which comprises an expression cassette, said expression cassette containing a DNA sequence coding for an amylosucrase.

The linear α-1,4 glucans formed in the transgenic plant cells and plants with the help of the amylosucrase can be isolated from transgenic plant cells and plants in the same manner as the starch which is normally formed. They are likewise an object of the present invention.

The invention furthermore relates to the use of the DNA sequences of the invention or parts thereof for the expression of a polypeptide having amylosucrase activity, preferably in microorganisms having no amylosucrase activity of their own. In this application, microorganisms are to be understood as bacteria as well as all protists such as defined by, e.g., Schlegel "Allgemeine Mikrobiologie" (Georg Thieme Verlag, 1985, pages 1–2). Today, biotechnological research to a large extent uses microorganisms to synthesize and process the most varied substances. This has become possible by the provision of a multitude of various systems for the efficient expression of procaryotic and eucaryotic genes in microorganisms (for an overview see, e.g., Methods in Enzymology 153:385–516). Widely used are, e.g. the strains of the bacterial species *Escherichia coli* and *Bacillus subtilis*. By providing the DNA sequences of the invention, particularly the DNA sequence depicted in Seq ID No. 1, it is now possible to express a protein having amylosucrase activity in microorganisms for which the appropriate expression systems are available.

The present invention particularly relates to a process for the production of microorganisms capable of synthesizing, either intracellularly or extracellularly, linear α-1,4 glucans, in which a DNA sequence of the invention is introduced and expressed in the microorganism. Such a process may exemplarily comprise the following steps:

(a) producing an expression cassette having the following partial sequences:
  (i) a promoter being active in the selected microorganism and ensuring transcription of the DNA sequence downstream thereof;
  (ii) a DNA sequence coding for an amylosucrase and being fused to the promoter in sense orientation;
  (iii) a transcription termination signal being functional in microorganisms;
(b) transforming an appropriate microorganism with the expression cassette constructed in step (a).

Expression vectors have been extensively described in the art. In addition to a selection marker gene and a replication origin allowing replication in the selected host they normally contain a bacterial or viral promoter and a transcription termination signal. Between promoter and termination signal there is at least one restriction site or one polylinker which allows insertion of a coding DNA sequence. As promoter sequence the DNA sequence which normally controls transcription of the corresponding gene can be used as long as it is active in the selected organism. This sequence can be replaced by other promoter sequences. Promoters can be used that effect constitutive expression of the gene or inducible promoters that allow a selective regulation of the expression of the gene downstream thereof. Bacterial and viral promoter sequences having these properties have been extensively described in the art. Promoters allowing a particularly strong expression of the gene downstream thereof, are, e.g., the T7 promoter (Studier et al., 1990, in Methods in Enzymology 185:60–89), lacuv5, trp, trp-lacUV5 (DeBoer et al., in Rodriguez, R. L. and Chamberlin, M. J., (Eds.), Promoters, Structure and Function; Praeger, N.Y., 1982, pp. 462–481; DeBoer et al., 1983, Proc. Natl. Acad. Sci. USA 80:21–25), $lp_1$, rac (Boros et al., 1986, Gene 42:97–100) or the ompF promoter. The DNA sequence mentioned in process step (a) (ii) can be any DNA sequence coding for a protein having the enzymatic activity of an amylosucrase. Preferably, DNA sequences derived from microorganisms, particularly gram negative bacteria, preferably from the genus Neisseria and particularly preferred from *Neisseria polysaccharea*, are used. In a particularly preferred embodiment the DNA sequence has the nucleotide sequence indicated under Seq ID No. 1 or a DNA sequence that hybridizes thereto and that codes for a protein having the enzymatic activity of an amylosucrase, with said sequence being linked to the promoter in sense direction (3' end of the promoter to the 5' end of the coding sequence).

The sequence used can be modified either before or after integration into the expression vector to vary, if necessary, the properties of the polypeptide or its localization, as described infra in more detail. Instead of the sequence indicated under Seq ID No. 1 DNA sequences can be used that can be derived from said sequence by substitution, insertion or deletion, as long as the enzymatic activity of the encoded protein is not impaired. The transformation of the microorganisms in step (b) can usually be carried out by standard techniques, such as described in Maniatis et al. (Molecular Cloning: A Laboratory Manual, 1982, New York: Cold Spring Harbor Laboratory Press). The transformed microorganism is cultivated in media that must be appropriate for the needs of the individual host used. Specific attention should be paid to pH value, temperature, ventilation, etc.

Another object of the invention are the microorganisms resulting from the process described above, which are characterized by containing a DNA sequence coding for an amylosucrase, with said sequence being part of a recombinant DNA molecule. Said recombinant DNA molecule— depending on the transformation method used—can be present in the cells either outside of the genome or can be stably integrated into the genome of the cells of the microorganism used.

The amylosucrase expressed by *Neisseria polysaccharea* is an extracellular enzyme which synthesizes linear α-1,4 glucans outside of the cells on the basis of sucrose. Unlike in the most pathways of synthesis for polysaccharides that proceed within the cell, neither activated glucose derivatives nor cofactors are required. The energy that is required for the formation of the α-1,4 glucosidic link between the condensed glucose residues is directly obtained from the hydrolysis of the link between the glucose and the fructose unit in the sucrose molecule. It is therefore possible to cultivate amylosucrase-secreting microorganisms, which were obtained by the process steps described above, in a sucrose-containing medium, with the secreted amylosucrase leading to a synthesis of linear α-1,4 glucans from sucrose in the medium. These glucans can be isolated from the culture medium. It is furthermore possible to synthesize α-1,4 glucans in vitro with the help of a cell-free enzyme preparation. In this case amylosucrase-secreting microorganisms are cultivated in a sucrose-free medium allowing expression of the amylosucrase until the stationary growth phase is reached. After removal of the cells from the growth medium by centrifugation the secreted enzyme can be obtained from the supernatant. The enzyme can then be added to sucrose-containing solutions to synthesize linear α-1,4 glucans. As compared to the synthesis of linear α-1,4 glucans directly in a sucrose-containing growth medium this method is advantageous in that the reaction conditions can be better controlled and that the reaction products are substantially purer and can more easily be further purified.

The enzyme can be purified from the culture medium by conventional purification techniques such as precipitation, ion exchange chromatography, affinity chromatography, gel filtration, HPLC reverse phase chromatography, etc. It is furthermore possible to express a polypeptide by modification of the DNA sequence inserted into the expression vector leading to a polypeptide which can be isolated more easily from the culture medium due to certain properties. It is possible to express the enzyme as a fusion protein along with another polypeptide sequence whose specific binding properties allow isolation of the fusion protein via affinity chromatography. Known techniques are, e.g., expression as fusion protein along with glutathion S transferase and subsequent purification via affinity chromatography on a glutathion column, making use of the affinity of the glutathion S transferase to glutathion (Smith and Johnson, 1988, Gene 67:31–40). Another known technique is the expression as fusion protein along with the maltose binding protein (MBP) and subsequent purification on an amylose column (Guan et al., 1988, Gene 67:21–30; Maina et al., 1988, Gene 74:365–373).

In addition to the possibility of directly adding the purified enzyme to a sucrose-containing solution to synthesize linear α-1,4 glucans, there is the alternative of immobilizing the enzyme on a carrier material. Such immobilization offers the advantage that the enzyme as synthesis catalyst can easily be retrieved and can be used several times. Since the purification of enzymes usually is very time and cost intensive, an immobilization and reuse of the enzyme contributes to a considerable reduction of the costs. Another advantage is the high degree of purity of the reaction products which inter alia is due to the fact that the reaction conditions can be better controlled when immobilized enzymes are used. The insoluble linear glucans yielded as reaction products can then be easily purified further. There are many carrier materials available for the immobilization of proteins which can be coupled to the carrier material either by covalent or non-covalent links (for an overview see: Methods in Enzymology Vol. 135, 136 and 137). Widely used carrier materials are, e.g., agarose, cellulose, polyacrylamide, silica or nylon.

In analogy to the purified enzyme, microorganisms expressing the desired polypeptide or secreting a specific metabolite can also be immobilized. Immobilization generally is achieved by inclusion of the cells in an appropriate material such as, e.g., alginate, polyacrylamide, gelatin, cellulose or chitosan. It is, however, also possible to adsorb or covalently bind the cells to a carrier material (Brodelius and Mosbach, in Methods in Enzymology, Vol. 135:173–175). An advantage of the immobilization of cells is that considerably higher cell densities can be achieved than by cultivation in a liquid culture, resulting in a higher productivity. Also the costs for agitation and ventilation of the culture as well as for the measures for maintaining sterility are reduced. An important aspect is that immobilization allows a continuous production so that long unproductive phases which usually occur in fermentation processes can be avoided or can at least be considerably reduced.

Like in microorganisms, the DNA sequences of the invention can also be used for the expression of an amylosucrase activity in fungi, in particular in yeasts, e.g., *Saccharomyces cerevisiae*. Vectors for the expression of heterologous genes in yeasts have been described (e.g., Bitter et al., 1987, Methods in Enzymology 153:516–544). These vectors, in addition to a selection marker gene and a replication origin for the propagation in bacteria, contain at least one further selection marker gene that allows identification of transformed yeast cells, a DNA sequence allowing replication in yeasts and a polylinker for the insertion of the desired expression cassette. The expression cassette is constructed from promoter, DNA sequence to be expressed and a DNA sequence allowing transcriptional termination and polyadenylation of the transcript. Promoters and transcriptional termination signals from Saccharomyces have also been described and are available. An expression vector can be introduced into yeast cells by transformation according to standard techniques (Methods in Yeast Genetics, A Laboratory Course Manual, Cold Spring Harbor Laboratory Press, 1990). Cells containing the vector are selected and propagated on appropriate selection media. Yeasts furthermore allow to integrate the expression cassette via homologous recombination into the genome of a cell using an appropriate vector, leading to a stable inheritance of the feature. Yeast strains expressing amylosucrase can be used in analogy to the microorganisms to obtain a secreted amylosucrase. Cultivation methods for yeasts have been sufficiently described (Methods in Yeast Genetics, A Laboratory Course Manual, Cold Spring Harbor Laboratory Press, 1990). Immobilization of the yeasts is also possible and is already used in the commercial production of ethanol (Nagashima et al., in Methods in Enzymology, Vol. 136:394–405; Nojima and Yamada, in Methods in Enzymology, Vol. 136:380–394). However, the use of yeasts secreting amylosucrase for the synthesis of linear α-1,4 glucans in sucrose-containing media is not readily possible as yeasts secrete an invertase that hydrolyzes extracellular sucrose. The yeasts import the resulting hexoses via a hexose transporter. Gozalbo and Hohmann (1990, Current Genetics 17, 77–79), however, describe a yeast strain that carries a defective suc2 gene and that therefore cannot secrete invertase. Also, these yeast cells do not contain a transport system for importing sucrose into the cells. If such a strain is modified with the DNA sequence of the invention such that it secretes an amylosucrase into the culture medium, linear α-1,4 glucans are synthesized by the amylosucrase if the culture medium contains sucrose. The fructose being formed as reaction product can subsequently be imported by the yeasts.

Therefore, the present invention also relates to a process for the production of fungal cells capable of synthesizing, either intracellularly or extracellularly, linear α-1,4 glucans in which a DNA sequence according to the invention is introduced into fungal cells and is expressed. Such a process may exemplarily comprise the following steps:

(a) producing an expression cassette having the following partial sequences:
   (i) a promoter being active in cells of the selected fungus and ensuring transcription of the DNA sequence downstream thereof,
   (ii) a DNA sequence coding for an amylosucrase and being fused to said promoter in sense orientation,
   (iii) a transcription termination signal being functional in said fungal cells; and (b) transforming fungal cells with the expression cassette constructed in step (a).

Another aspect of the present invention is the possibility of producing in an inexpensive manner pure fructose syrup by using the DNA sequences of the invention. Conventional methods for the production of fructose either contemplate the enzymatic hydrolysis of sucrose using an invertase or the degradation of starch into glucose units, often by acidolysis, and subsequent enzymatic conversion of the glucose into fructose by glucose isomerase. Both methods result in mixtures of glucose and fructose. The two components have to be separated from each other by chromatographic processes. The production of pure fructose or pure fructose syrup using a protein having the enzymatic activity of an amylosucrase is preferably carried out in a cell-free system using the purified enzyme. The latter can be immobilized on an appropriate carrier material or can be present in soluble form. The presence of sucrose results in a synthesis of linear glucans and in the release of fructose. Separation of the substrate from the reaction products or separation of the two reaction products can be achieved by, e.g., using membranes allowing the permeation of fructose but not of sucrose or glucans. If the fructose is continuously removed via such a membrane, the sucrose is converted more or less completely into fructose and linear glucans. Also the amylosucrase can preferably be immobilized on a carrier material located between two membranes, one of which allows the permeation of fructose but not of sucrose or glucans and the other allows the permeation of sucrose but not of glucans. The substrate is supplied through the membrane which allows the permeation of sucrose. The synthesized glucans remain in the space between the two membranes and the released fructose can continuously be removed from the reaction equilibrium through the membrane which allows only the permeation of fructose. Such a set-up allows an efficient separation of the reaction products and thus inter alia the production of pure fructose. The use of amylosucrases for the production of pure fructose offers the advantage that the comparably inexpensive substrate sucrose can be used as starting material and furthermore that the fructose can be isolated from the reaction mixture in a simple manner without chromatographic processes. The invention therefore also relates to the use of proteins having the enzymatic activity of amylosucrase for the production of fructose.

A further possibility of the use of proteins having amylosucrase activity is to use them for the production of cyclodextrins. Cyclodextrins are produced by the degradation of starch by the enzyme cyclodextrin transglycosylase (EC 2.4.1.19) which is obtained from the bacterium *Bacillus macerans*. Due to the branching of starch only about 40% of the glucose units can be converted to cyclodextrins using this system. By providing substantially pure proteins having amylosucrase activity it is possible to synthesize cyclodextrins on the basis of sucrose under the simultaneous action of amylosucrase and cyclodextrin transglycosylase, with the amylosucrase catalyzing the synthesis of linear glucans from sucrose and the cyclodetxtrin transglycosylase catalyzing the conversion of these glucans into cyclodextrins.

The plasmid pNB2 of the invention was deposited at Deutsche Sammlung von Mikroorganismen (DSM), Braunschweig, Germany, on May 6, 1994 according to the provisions of the Budapest Treaty under deposit no. DSM 9196.

| Abbreviations used | |
|---|---|
| IPTG | isopropyl β-D-thiogalacto-pyranoside |
| Media and solutions used | |
| YT medium | 8 g bacto-tryptone |
| | 5 g yeast extract |
| | 5 g NaCl |
| | ad 1000 ml with ddH$_2$O |
| YT plates | YT medium with 15 g bacto-agar/ 1000 ml |
| Lugol's solution | 12 g KI |
| | 6 g I$_2$ |
| | ad 1.8 l with ddH$_2$O |

The examples serve to illustrate the invention.

EXAMPLE 1

Isolation of a Genomic DNA Sequence Coding for an Amylosucrase Activity from *Neisseria polysacharea*

For the isolation of a DNA sequence coding for an amylosucrase activity from *Neisseria polysaccharea* first a genomic DNA library was established. *Neisseria polysaccharea* cells were cultured on "Columbia blood agar" (Difco) for 2 days at 37° C. The resulting colonies were harvested from the plates. Genomic DNA was isolated according to the method of Ausubel et al. (in: Current Protocols in Molecular Biology (1987), J. Wiley & Sons, NY) and processed. The DNA thus obtained was partially digested with the restriction endonuclease Sau3A. The resulting DNA fragments were ligated into the BamHI digested vector pBluescript SK(−). The ligation products were transformed in *E. coli* XL1-Blue cells. For their selection, the cells were plated onto YT plates with ampicillin as selection marker. The selection medium additionally contained 5% sucrose and 1 mM IPTG. After incubation over night at 37° C. the bacterial colonies that had formed were stained with iodine by placing crystalline iodine into the lid of a petri dish and placing the culture dishes with the bacteria colonies for 10 min each conversely onto the petri dish. The iodine which evaporated at room temperature stained some regions of the culture dishes that contained amylose-like glucans blue. From bacteria colonies that showed a blue corona plasmid DNA was isolated according to the method of Birnboim & Doly (1979, Nucleic Acids Res. 7:1513–1523). Said DNA was retransformed in *E. coli* SURE cells. The transformed cells were plated onto YT plates with ampicillin as selection marker. Positive clones were isolated.

EXAMPLE 2

Sequence Analysis of the Genomic DNA Insert of the Plasmid pNB2

Figure 1:
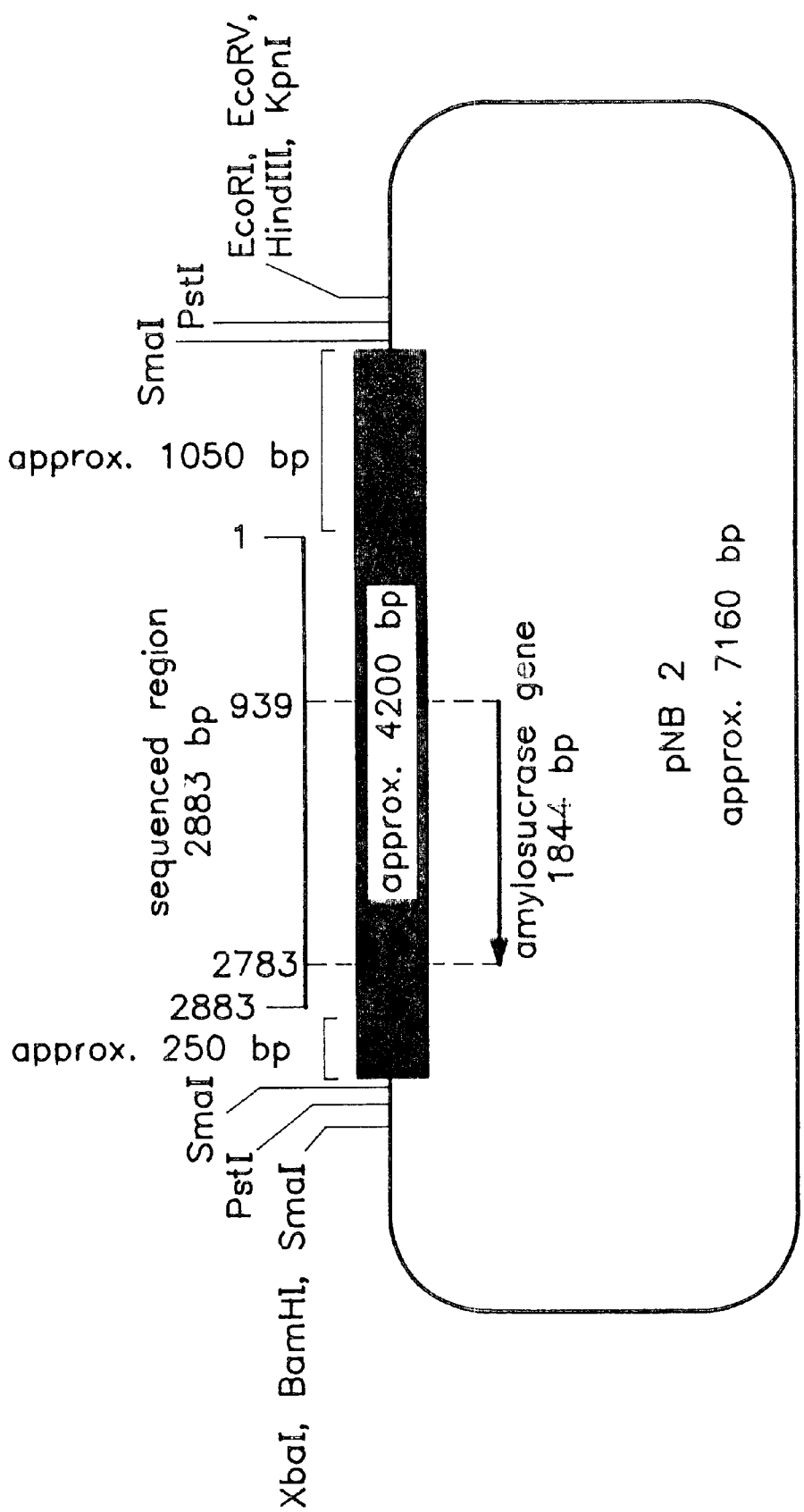
FIG. 1 shows the plasmid pNB2 (DSM 9196) The thin line corresponds to the sequence of the cloning vector pBluescript SK(−). The thick line represents the approx. 4.2 kb long insert of genomic DNA of *Neisseria polysaccharea*. The coding region for amylosucrase is depicted in form of an arrow below the insert. Above the insert the sequenced region is depicted. All numerical values refer to this 2883 bp long region.

From an *E. coli* clone obtained according to working example 1 a recombinant plasmid was isolated. Restriction analyses showed that said plasmid was a ligation product consisting of two vector molecules and an approx. 4.2 kb long genomic fragment. The plasmid was digested with the restriction endonuclease PstI and the genomic fragment was isolated (GeneClean, Bio101). The fragment thus obtained was ligated into a pBluescript II SK vector linearized with PstI, resulting in a duplication of the PstI and SmaI restriction sites. The ligation product was transformed in *E. coli* cells and the latter were plated on ampicillin plates for selection. Positive clones were isolated. From one of these clones the plasmid pNB2 (FIG. 1) was isolated and part of the sequence of its genomic DNA insert was determined by standard techniques using the dideoxy method (Sanger et al., 1977, Proc. Natl. Acad. Sci. USA 74:5463–5467). The entire insert is approx. 4.2 kbp long. The nucleotide sequence was determined from a partial sequence having a length of 2883 bp. This nucleotide sequence is indicated infra (seq ID No. 1). The localization of the sequenced region in the genomic insert is indicated in FIG. 1.

EXAMPLE 3

Figure 2:
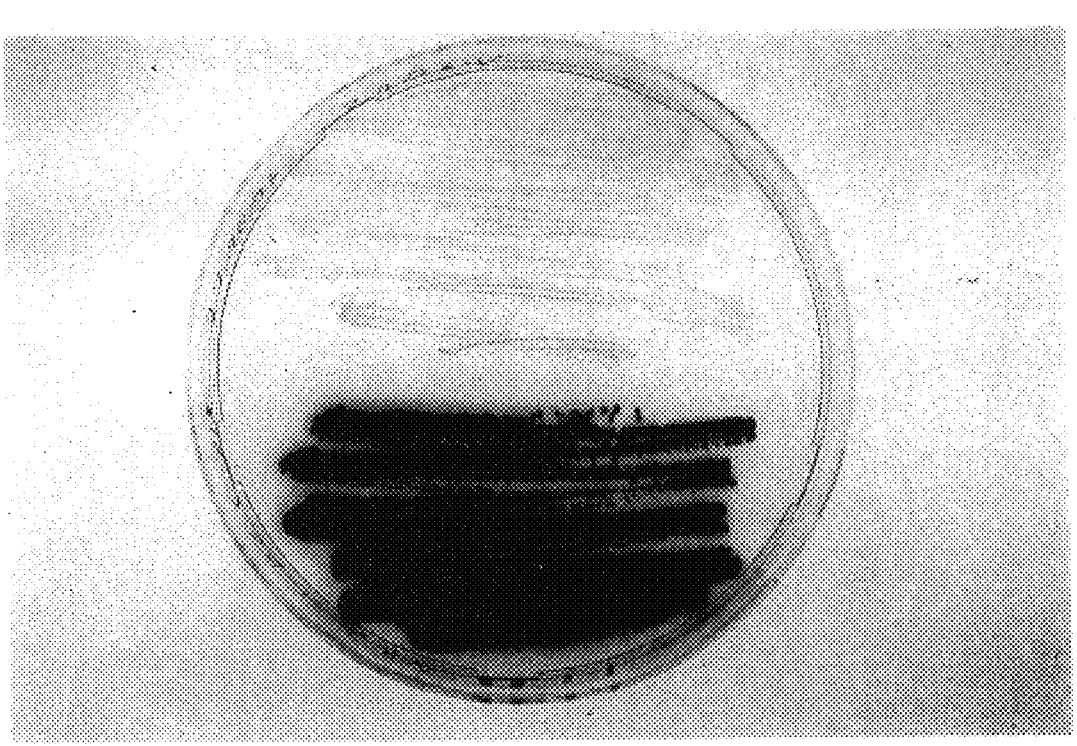
FIG. 2 shows the expression of an amylosucrase activity in transformed *E. coli* cells by subjecting them to iodine vapor. *E. coli* cells that have been transformed with the pBluescript II SK plasmid (A) and *E. coli* cells that have been transformed with the plasmid pNB2 (B) were plated on YT plates (1.5% agar; 100 μg/ml ampicillin; 5% sucrose; 0.2 mM IPTG) and incubated over night at 37° C. Then, the plates were subjected to iodine vapor. Colonies of the cells that were transformed with the plasmid pNB2 showed a distinct blue corona.

Expression of an Extracellular Amylosucrase Activity in Transformed *E. coli* Cells (a) Detection of an Amylosucrase Activity During Growth on YT Plates For the expression of an extracellular amylosucrase activity, *E. coli* cells were transformed with the vector pNB2 according to standard techniques. A colony of the transformed strain was incubated on YT plates (1.5% agar; 100 µg/ml ampicillin; 5% sucrose; 0.2 mM IPTG) over night at 37° C. The amylosucrase activity was detected by subjecting the colonies to iodine vapor (FIG. 2). Amylosucrase-expressing colonies exhibit a blue corona. Amylosucrase activity can be observed even if no IPTG was present, probably due to the activity of the endogenous amylosucrase promoters.

(b) Detection of an Amylosucrase Activity During Growth in YT Medium

For the expression of an extracellular amylosucrase activity, E. coli were transformed with the vector pNB2 according to standard techniques. YT medium (100 µg/ml ampicillin; 5% sucrose) was inoculated with a colony of the transformed strain. The cells were incubated over night at 37° C. under constant agitation (rotation mixer; 150–200 rpm). The products of the reaction catalyzed by amylosucrase were detected by adding Lugol's solution to the culture supernatant, leading to blue staining.

(c) Detection of the Amylosucrase Activity in the Culture Supernatants of Transformed E. coli Cells Which Were Cultivated Without Sucrose For the expression of an extracellular amylosucrase activity, E. coli cells were transformed with the vector pNB2 according to standard techniques. YT medium (100 µg/ml ampicillin) was inoculated with a colony of the transformed strain. The cells were incubated over night at 37° C. under constant agitation (rotation mixer; 150–200 rpm). Then the cells were removed by centrifugation (30 min, 4° C., 5500 rpm, JA10 Beckmann rotor). The supernatant was filtered through a 0.2 µm filter (Schleicher & Schuell) under sterile conditions.

Detection of an amylosucrase activity was carried out by (i) incubating the supernatant on a sucrose-containing agar plate. 40 µl of the supernatant were placed in a whole punched into an agar plate (5% sucrose in 50 mM sodium citrate buffer pH 6.5) and incubated at least for one hour at 37° C. The products of the reaction catalyzed by amylosucrase were detected by staining with iodine vapor. Presence of the reaction products produces a blue stain.

(ii) or by gel electrophoretic separation of the proteins of the supernatant in a native gel and detection of the reaction products in the gel after incubation with sucrose. 40–80 µl of the supernatant were separated by gel electrophoresis on an 8% native polyacrylamide gel (0.375 M Tris pH 8.8) at a voltage of 100 V. The gel was then twice equilibrated 15 min with approx. 100 ml 50 mM sodium citrate buffer (pH 6.5) and incubated over night at 37° C. in sodium citrate buffer pH 6.5/5% sucrose. In order to make the reaction product of the reaction catalyzed by amylosucrase visible, the gel was rinsed with Lugol's solution. Bands having amylosucrase activity were stained blue.

EXAMPLE 4

In vitro Production of Glucans with Partially Purified Amylosucrase

For the expression of an extracellular amylosucrase activity, E. coli cells were transformed with the vector pNB2 according to standard techniques. YT medium (100 µg/ml ampicillin) was inoculated with a colony of the transformed strain. The cells were incubated over night at 37° C. under constant agitation (rotation mixer; 150–200 rpm). Then the cells were removed by centrifugation (30 min, 4° C., 5500 rpm, JA10 Beckmann rotor). The supernatant was filtered through a 0.2 µm filter (Schleicher & Schuell) under sterile conditions. The supernatant was then concentrated by 200 times using an Amicon chamber (YM30 membrane having an exclusion size of 30 kDa, company Amicon) under pressure (p=3 bar). The concentrated supernatant was added to 50 ml of a sucrose solution (5% sucrose in 50 mM sodium citrate buffer pH 6.5). The entire solution was incubated at 37° C. Whitish insoluble polysaccharides are formed.

EXAMPLE 5

Characterization of the Reaction Products Synthesized by Amylosucrase from Example 4

The insoluble reaction products described in Example 4 are soluble in 1 M NaOH. The reaction products were characterized by measuring the absorption maximum. Approx. 100 mg of the isolated reaction products (wet weight) were dissolved in 200 µl 1 M NaOH and diluted with $H_2O$ 1:10. 900 µl of 0.1 M NaOH and 1 ml Lugol's solution were added 100 µl of this dilution. The absorption spectrum was measured between 400 and 700 nm. The maximum is 605 nm (absorption maximum of amylose: approx. 614 nm). HPLC analysis of the reaction mixture of Example 4 on a CARBOPAC PA1 column (DIONEX) showed that in addition to the insoluble products soluble products were also formed. These soluble products are short-chained polysaccharides. The chain length was between approx. 5 and approx. 60 glucose units. To a smaller extent, however, even shorter or longer molecules could be detected. With the available analytical methods it was not possible to detect branching in the synthesis products.

EXAMPLE 6

Expression of an Intracellular Amylosucrase Activity in Transformed E. coli Cells Using a polymerase chain reaction (PCR) a fragment was amplified from the plasmid pNB2 which comprises the nucleotides 981 to 2871 of the sequence depicted in Seq ID No. 1. The following oligonucleotides were used as primers:

TPN2 5'-CTC ACC ATG GGC ATC TTG GAC ATC-3' (Seq ID No. 3)
TPC1 5'-CTG CCA TGG TTC AGA CGG CAT TTG G-3' (Seq ID No. 4)

The resulting fragment contains the coding region for amylosucrase except for the nucleotides coding for the 16 N-terminal amino acids. These amino acids comprise the sequences that are necessary for the secretion of the enzyme from the cell. Furthermore, this PCR fragment contains 88 bp of the 3' untranslated region. By way of the primers used NcoI restriction sites were introduced into both ends of the fragment. After digestion with the restriction endonuclease NcoI the resulting fragment was ligated with the NcoI digested expression vector pMex 7. The ligation products were transformed in E. coli cells and transformed clones were selected. Positive clones were incubated over night at 37° C. on YT plates (1.5% agar; 100 µg/ml ampicillin; 5% sucrose; 0.2 mM IPTG). After subjecting the plates to iodine vapor no blue staining could be observed in the area surrounding the bacteria colonies, but the intracellular production of glycogen could be detected (brown staining of transformed cells in contrast to no staining in nontransformed XL1-Blue cells). In order to examine the functionality of the protein, transformed cells cultivated on YT medium were broken up by ultrasound and the obtained crude extract was pipetted onto sucrose-containing agar plates. After subjecting the plates to iodine vapor a blue stain could be observed.

What is claimed is:

1. An isolated DNA molecule comprising a DNA sequence encoding a protein having the enzymatic activity of an amylosucrase, wherein said DNA sequence is selected from the group consisting of
   (a) a DNA sequence coding for a protein having Seq ID No 2;
   (b) the coding region of Seq ID No. 1,
   (c) a DNA sequence in the DNA insert of plasmid pNB2 from Neisseria bacteria having deposit number Deutsche Sammlung von Mikroorganismen (DSM) No. 9196;
   (d) a DNA sequence coding for a protein encoded by the DNA insert of plasmid pNB2 from Neisseria bacteria having deposit number Deutsche Sammlung von Mikroorganismen No. 9196;
   (e) a DNA sequence which is degenerate due to the genetic code in comparison to the sequences of (b), (c), or (d);
   (f) a part of any one of the DNA sequences of (a)–(e) coding for a protein having the enzymatic activity of an amylosucrase; and
   (g) a full length complement of the DNA sequence of any one of (a)–(f).

2. A recombinant DNA molecule comprising the DNA molecule according to claim 1.

3. The recombinant DNA molecule according to claim 2, wherein the DNA sequence coding for a protein having the enzymatic activity of an amylosucrase is linked to DNA sequences allowing transcription in procaryotic or eucaryotic cells.

4. A process for the production of a protein having the activity of an amylosucrase, comprising the step of culturing a microorganism or a fungal cell comprising an exogenous recombinant DNA molecule comprising the DNA molecule according to claim 1 or 3 in a suitable culture medium and expressing the DNA molecule coding for the protein in said microorganism or fungal cell.

5. A microorganism comprising an exogenous recombinant DNA molecule comprising the DNA molecule according to claim 1.

6. A fungal cell comprising an exogenous recombinant DNA molecule comprising the DNA molecule according to claim 1.

7. A process for the production of a transgenic plant, comprising the steps of introducing the DNA molecule according to claim 1 or into a plant cell and regenerating the transgenic plant from said plant cell.

8. A process for the production of a transgenic plant, comprising the steps of:
   (a) producing an expression cassette comprising the following DNA sequences:
      (i) a promoter that is active in plants and ensures formation of an RNA in target tissue or target cells;
      (ii) the DNA molecule according to claim 1 which is fused to the promoter in sense orientation; and
      (iii) a signal functional in plants for the transcription termination and polyadenylation of an RNA molecule,
   (b) transferring the expression cassette into a plant cell, and
   (c) regenerating the transgenic plant from the transformed plant cell.

9. A process for the production of a microorganism capable of synthesizing linear α-1,4 glucans, comprising the step of introducing the DNA molecule according to claim 1 into the microorganism.

10. A process for the production of a microorganism capable of α-1,4 glucans, comprising the steps of: synthesizing linear
    (a) producing an expression cassette comprising the following DNA sequences:
       (i) the DNA molecule according to claim 1,
       (ii) a promoter active in the selected microorganism to ensure transcription of the DNA molecule, wherein the DNA molecule is fused in sense orientation downstream of the promoter,
       (iii) a transcription termination signal functional in the microorganism, and
    (b) transforming the microorganism with the expression cassette constructed in step (a).

11. A process for the production of a fungal cell capable of synthesizing linear α-1,4 glucans, comprising the step of introducing the DNA molecule according to claim 1 into the fungal cell.

12. A process for the production of a fungal cell capable of synthesizing linear α-1,4 glucans, comprising the steps of:
    (a) producing an expression cassette comprising the DNA sequences
       (i) the DNA molecule according to claim 1,
       (ii) a promoter active in the fungal cell to ensure transcription of the DNA molecule, wherein the DNA molecule is fused in sense orientation downstream of the promoter;
       (iii) a transcription termination signal functional in said fungal cell, and
    (b) transforming the fungal cell with the expression cassette constructed in step (a).

13. A transgenic plant comprising an exogenous recombinant DNA molecule comprising the DNA molecule according to claim 1.

14. The plant according to claim 13, characterized in that said plant is a crop plant.

15. The plant according to claim 13 or 14, characterized in that said plant is a maize, rice, wheat, barley, sugar beet, sugar cane, tobacco, tomato or potato plant.

16. A transgenic plant cell comprising an exogenous recombinant DNA molecule comprising a DNA molecule according to claim 1.

17. A vector comprising the isolated DNA molecule of claim 1.

18. The plasmid pNB2, deposited as DSM 9196.

19. An isolated DNA molecule comprising a first DNA sequence encoding a protein having the enzymatic activity of an amylosucrase, wherein said first DNA sequence is more than 60% homologous to a second DNA sequence selected from the group consisting of:

(a) a DNA sequence coding for a protein having Seq ID No 2;
(b) the coding region of Seq ID No. 1,
(c) a DNA sequence encoding a protein having amylosucrase activity in the DNA insert of plasmid pNB2 from Neisseria bacteria having deposit number Deutsche Sammlung von Mikroorganismen (DSM) No 9196,
(d) a DNA sequence coding for a protein encoded by the DNA insert of plasmid pNB2 from Neisseria bacteria having deposit number Deutsche Sammlung von Mikroorganismen No. 9196;
(e) a part of any one of the DNA sequences of (a)–(d) coding for a protein having the enzymatic activity of an amylosucrase; and
(f) a full length complement of the DNA sequence of any one of (a)–(e).

20. The DNA molecule according to claim 19, wherein the first DNA sequence is more than 80% homologous to the second DNA sequence selected from the group consisting of (a)–(f).

21. The DNA molecule according to claim 19, wherein the first DNA sequence is more than 95% homologous to the second DNA sequence selected from the group consisting of (a)–(f).

22. A microorganism comprising an exogenous recombinant DNA molecule comprising the DNA molecule according to any one of claims 19–21.

23. A fungal cell comprising an exogenous recombinant DNA molecule comprising the DNA molecule according to any one of claims 19–21.

24. The plant according to any one of claims 13, 14 or 23, characterized in that said plant is a maize, rice, wheat, barley, sugar beet, sugar cane, tobacco, tomato or potato plant.

25. A vector comprising the isolated DNA molecule according to any one of claims 1, 2, 3, 16, 17, 18 or 19.

* * * * *

UNITED STATES PATENT AND TRADEMARK OFFICE
CERTIFICATE OF CORRECTION

PATENT NO.    : 6,265,635 B1
DATED         : July 24, 2001
INVENTOR(S)   : Jens Kossmann, Volker Buttcher and Thomas Welsh It is certified that error appears in the above-identified patent and that said Letters Patent is hereby corrected as shown below:

<u>Title page,</u>
Item [73], change the name of the assignee from "Plantec Biotechnologie GmbH" to
-- PlantTec Biotechnologie GmbH --.

Signed and Sealed this

Eighteenth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,265,635 B1 Page 1 of 1
APPLICATION NO. : 08/737752
DATED : July 24, 2001
INVENTOR(S) : Jens Kossmann, Volker Buttcher and Thomas Welsh It is certified that error appears in the above-identified patent and that said Letters Patent is hereby corrected as shown below:

Column 29,
Line 44, change "claim 1 or 3" to -- claim 1 or 2 --.
Line 55, delete "or" after "claim 1".

Column 30,
Line 32, change "capable of α-1,4 glucans, comprising the steps of: synthesizing linear" to -- capable of synthesizing linear α-1,4 glucans, comprising the steps of: --.
Line 54, change "according to claim 13 or 14" to -- according to any one of claims 13, 14 or 24 --.
Lines 60-61, delete entire claim and replace with -- A transgenic plant cell comprising an exogenous recombinant DNA molecule comprising a DNA molecule according to any one of claims 19-21. --.

Column 32,
Line 7, change "claims 1, 2, 3, 16, 17, 18 or 19" to -- claims 1, 2, 3, 18, 19, 20 or 21. --.
Lines 12-15, delete entire claim and replace with -- A transgenic plant comprising an exogenous recombinant DNA molecule comprising a DNA molecule according to any one of claims 19-21. --.

Signed and Sealed this

Twenty-seventh Day of June, 2006

JON W. DUDAS
*Director of the United States Patent and Trademark Office*